(12) United States Patent
McCready et al.

(10) Patent No.: US 8,979,710 B2
(45) Date of Patent: Mar. 17, 2015

(54) ADAPTABLE EXERCISE SYSTEM AND METHOD

(71) Applicants: Joshua McCready, San Francisco, CA (US); Alexander Gourley, San Francisco, CA (US)

(72) Inventors: Joshua McCready, San Francisco, CA (US); Alexander Gourley, San Francisco, CA (US)

(73) Assignee: Active Theory Inc., Berkeley, CA (US)

( * ) Notice: Subject to any disclaimer, the term of this patent is extended or adjusted under 35 U.S.C. 154(b) by 172 days.

(21) Appl. No.: 13/843,865

(22) Filed: Mar. 15, 2013

(65) Prior Publication Data

US 2014/0274567 A1    Sep. 18, 2014

(51) Int. Cl.
*A63B 71/00* (2006.01)
*A63B 24/00* (2006.01)

(52) U.S. Cl.
CPC .................................. *A63B 24/0059* (2013.01)
USPC ............................................................ 482/8

(58) Field of Classification Search
CPC ........... A63B 71/0619; A63B 71/0622; A63B 71/0638; A63B 71/0644
USPC .................. 482/1, 3–9, 901, 902; 463/30–34; 348/77
See application file for complete search history.

(56) References Cited

U.S. PATENT DOCUMENTS

| | | | |
|---|---|---|---|
| 8,075,450 B2* | 12/2011 | Fabbri et al. | 482/8 |
| 8,083,647 B2* | 12/2011 | Park | 482/8 |
| 2008/0022348 A1* | 1/2008 | Shen | 725/135 |
| 2012/0046144 A1* | 2/2012 | Lin et al. | 482/8 |
| 2013/0190135 A1* | 7/2013 | Pryor | 482/8 |

* cited by examiner

*Primary Examiner* — Oren Ginsberg

(57) ABSTRACT

A system and method for correlating a video content presentation rate with an exercise machine operation rate is disclosed. A preferred embodiment of the apparatus is an interactive video system that adapts easily to use with a wide range of gym equipment utilizing a video presentation device that includes an accelerometer and/or camera. The camera embodiment utilizes vision algorithms to determine periodicity and motion orientation prior to modifying the input as a function of the type of exercise equipment is being utilized, in order to determine a cadence. In one embodiment the camera does not rely on seeing the limbs being exercised but utilizes the observation that even highly trained athletes have a degree of extraneous motion of their theoretically immobile body parts during exercise. A prerecorded video presentation is modulated by sensing proximate vibrational energy to determine cadence in the case of the accelerometer.

30 Claims, 2 Drawing Sheets

ADAPTABLE EXERCISE SYSTEM AND METHOD

This application claims the benefit of U.S. provisional patent applications 61/615,758 (METHOD AND PROGRAM FOR TRACKING AND DETERMINING REGIONS OF COHESIVE MOTION BETWEEN IMAGES) and 61/615,754 (MOTION TRACKING SYSTEM FOR EXERCISE)

FIELD OF THE INVENTION

This invention relates generally to video presentation and exercise machines and specifically to adapting video display devices to operate interactively with a plurality exercise machines.

BACKGROUND

People who use exercise machines (e.g. exercise bicycles, rowing machines, treadmills weight machines, steppers and the like) increasingly perform these activities while watching a video presentation that mimics the sights and/or sounds of traveling through a remote location (hereafter called "forward motion video"), playing a video game or navigating digital content. By engaging the mind in these ways users tend to exercise for longer periods of time, with increased vigor and to perform the exercise more consistently. Such prior art systems include a video display and exercise equipment with at least one sensor mounted to the equipment or to the user so that the activity level may be determined by a feedback mechanism enabling a processor to control the video presentation as a function of user activity. Prior art examples:

U.S. Pat. No. 4,720,789 to Hector et al. discloses a video game, or an exercise system utilizing a video display, that is played by movement of the game player's feet. The apparent objective is to require the game player to exercise while playing the game by moving his feet. However, the game player is required to move at the game's speed. The game in no way alters to conform to the individual's fitness level.

U.S. Pat. No. 4,278,095 to Lapeyre discloses an exercise device connected to a video machine. The speed of the exercise device, and the accompanying video display, is controlled by the exerciser. As the exerciser signals an increase in speed to the exercise device, an accompanying signal is sent to the video machine, so that the exerciser is presented with a visual display of the increase in speed. The exercisers heart rate is monitored and displayed on a T.V. monitor.

U.S. Pat. No. 4,512,567 to Phillips discloses an exercise bicycle used to operate a video game. The game player receives exercise while operating the bicycle, and at the same time, moving the handlebars. The video game operates at a preset speed, thus making no allowance for the fitness of the player.

U.S. Pat. No. 4,630,817 to Buckley discloses an exercise machine that allows for movement of a control rod, e.g., a handlebar, to provide two degrees of freedom to a controllable character in a video display. Resistance is provided to the handlebar to ensure that physical exertion is required by the user.

U.S. Pat. No. 5,001,632 to Hall-Tipping discloses a combination of a video game system and an exercise device whereby the play action of the video game is controlled by reference to the exercisers heart rate and the output level of the exercise device.

U.S. Pat. No. 5,362,069 to Hall-Tipping discloses an apparatus which couples an exercise device to a video game in which the heart rate of the user (aerobic level) and the exercise device output level (bicycle pedal rate) are coupled to a standard video game in addition to the normal game hand controls. The video game difficulty and game piece movement level as well as the pedal resistance are changed in response to the heart rate signal in order to keep the user exercising at the desired or programmed rate.

U.S. Pat. No. 5,385,519 to Hsu et al discloses a computer controlled running machine which tilts and changes endless belt speed in synchronization with a computer CD programmed with various road conditions and sounds. The CD provides visual images and sounds of the road to the user via a head mounted visual-acoustic mask. There is no mechanism to vary the visual or audio effects due to the activity of the user.

U.S. Pat. No. 5,246,411 to Rackman et al discloses an exercise bike coupled through a speed sensor and a noise generator to a TV to introduce noise into the TV channel if the user exercises below a preset level or above another preset level.

U.S. Pat. No. 5,240,417 to Smithson et al discloses an arcade type bicycle racing simulation device which visually portrays, in an animated video scene, a riders movements on an exercise bike in response to a variable terrain in the computer generated animated video. Sensors on the bicycle sense pedal speed and leaning position and feed this information to a computer which uses computer animation to change the position of an animated figure in the video scene of the track.

U.S. Pat. No. 5,277,678 to Friedebach et al discloses a skiing simulation device that is coupled to a video display which shows images of the terrain that the skier is moving over. The video system such as a video tape may send control signals to servo-motors to increase or decrease resistance to the movement of the skates depending on the viewed terrain on the tape.

U.S. Pat. No. 5,308,296 discloses an interactive exercise device that utilizes interactive compact disc driven adventure scenarios and the users physical responses to generate different outcomes to the computer generated scenarios presented on the video monitor. Speed and timing of exercise actions are required in order to advance through the scenario program.

U.S. Pat. No. 5,462,503 to Benjamin et al and U.S. Pat. No. 5,466,200 to Ulrich et al disclose a networked computer generated environment through which one or more users navigate on an exercise device such as a recumbent exercise bicycle with pedals and a steering control. The computer controls the resistance against pedaling and generates display of the relative positions of the networked users in the computer generated environment.

U.S. Pat. No. 6,004,243 Hall-Tipping discloses a combination of a video game system and an exercise device whereby the play action of the video game is controlled by reference to the users heart rate and the output level of the exercise device with the ability to regulate both the exercise device and the play of a video game according to the activity level of an exerciser.

U.S. Pat. No. 6,004,243 to Ewert discloses a visual-image stream a prerecorded scene or a graphically generated scene replayed from commonly available analog and digital visual-image storage devices, such as a videotape, a compact disk (CD), a digital video disk (DVD), or other storage devices. Alternatively, the visual-image stream may be a recording that the user made of a favorite course or jogging trail. To make exercise more interesting, exercisers want to more closely simulate outdoor exercise.

U.S. Pat. No. 6,004,243 to Ewert, discloses a forward motion video controlled by a sensor that may be adapted to different exercise machines.

U.S. Pat. No. 6,142,913 to Ewert discloses real-time augmentation of forward motion video but requires extensive sensors network to be attached to the exercise machine.

20050075213 to Arick discloses forward-motion video controlled by a sensor, such as pedometer or accelerometer, mounted to the user.

However, the prior art falls short of providing the desired functionality because oftentimes users will exercise on multiple machines in a single visit to the gym. These different machines will include different exercise modalities, such as rowing, walking, cycling, stair climbing, weightlifting, etc., modalities which include different motions and utilize different parts of the body in different ways. Buttons and text are usually too small to use while exercising. Another problem with forward motion video and gaming in the exercise context is that it is inconsistent with the goal of following a particular exercise regimen.

It is therefore desirable to provide a system that enables users to exercise on a variety of machines while receiving the benefits provided by forward motion video, gaming and/or viewing digital content that is responsive to the exercise performed and/or the ability to interact with or guide a video presentation while continuing to perform these exercises. Furthermore, it is desirable that the sensing technology(ies) be capable of operating on different machines, especially to do so without requiring physical set up or customization and furthermore to do so with minimal software set up. It is desirable to provide a system that can be moved from machine to machine quickly and easily. It is desirable to provide a system that can be adapted for use on different machines by modifying software rather than modifying hardware. Furthermore, it is desirable to leave the user unencumbered by sensors on their person, both to minimize the weight and restriction but also to avoid the risk of physical harm caused by a sensor catching on or otherwise interfering with the exercise equipment during use. Yet furthermore, it is desirable to provide a system that can be used in an environment that is visually dynamic and acoustically noisy. Furthermore, it is desirable to provide means for a forward motion video exercise system to receive input from a user whose hands and feet may be preoccupied with exercise activities.

SUMMARY

Embodiments of this invention may be advantageously configured to provide: means to control forward motion video, video games and to view and/or control digital content in such a way that the video display easily adapts for operation with a variety of exercise machines commonly used in gyms: machines that have been task-designed, allowing a user to row, walk, cycle, climb stairs, lift weights to exercise a specific muscle group, and the like; to control forward motion video, video games and digital content with a video display system that may be readily moved to a variety of such exercise machines; to control forward motion video, games and to navigate files such as personal photos and video memorabilia while using such exercise equipment by utilizing different parts of the body, including the legs, arms, hands, torso and head as the control mechanism; to control forward motion video, games and the ability to view digital content while using such exercise equipment without encumbering the user's body with sensors attached thereto; to improve the exercise experience by modifying visual content viewed while exercising in novel ways so that it correlates with sensed activity, beyond merely modifying the speed of presentation; to perform the above tasks without requiring set up or adjustment, especially if not more than indicating to the system the type of exercise to be performed; to provide reliable operation individually and acoustically noisy environments; and to artificially manipulate video presentation to achieve a desired exercise regimen or profile.

In one embodiment the system utilizes a display device such as a tablet, laptop computer or smart phone with a camera built into the same housing. The camera can be a CCD, CMOS, analog, RGBD, or any other at a distance sensor. The camera is oriented toward the user, however the camera does not need to be pointed directly to the limbs being exercised. Limb can mean arms, legs, head or torso. For example, when someone is using a bike their head will show cyclical motion at the same rhythm at which their legs are pedaling. This is an important feature because the shelves built into exercise devices are intended to hold a book or magazine in an orientation so the exerciser may see it easily while exercising. These shelves therefore are relatively high and angled to face upwards, away from the view of the limbs being exercised. There is a mutual exclusivity between the user viewing the screen properly with the device angled upwards and tilting the camera (often built into the display of the device) downwards in order to view the legs of the user. Therefore, in one embodiment the system relies on the observation that even highly trained athletes have a degree of extraneous motion of their theoretically immobile body parts during exercise. In one embodiment the camera is extrapolating cadence data from determining the periodicity of small motions of head and torso. (Note: "cadence" will always be referred to in this document as the exercise rate and "periodicity" will always be referred to as the frequency of any motion being sensed, which may not be the same as the exercise rate.) On this point, in one embodiment the camera is extrapolating cadence data from body parts that are not directly associated with the cadence. Depending on the form of exercise, this extrapolated data sometimes requires a correction factor between the small motion periodicity and the true cadence. For example, in cycling the true cadence is a one-to-one ratio with the small motion periodicity. In treadmill, and most ambulatory exercise machines the true cadence is a 1:2 ratio with the small motion periodicity. In one embodiment, the output from the camera is interpreted by the system in its entirety, meaning it is viewing the entire scene simultaneously without differentiation. In one embodiment, the system is identifying edges and/or regions of motion and tracking those features as user features. In a further variant of that embodiment the system tracks features entering the field of view distal to said user features, and rejects them for influence to the system.

In one embodiment, the user will tell the system the type of exercise; however, depending on the exercise being performed the small motion periodicity will be vertical or horizontal. In cycling the small motion periodicity is horizontal in orientation whereas on the treadmill and rowing machines, the small motion periodicity is vertical. This data may be used for the system to determine which exercise is being performed.

In one embodiment the intensity of exercise is determined using an accelerometer or microphone. As the user increases the level of exercise intensity the vibrational energy increases. In one embodiment, the system establishes a preliminary top-end range based on historical data, and seeks to scale the measured input as a function of the measured energy to linearize the input. If the user exceeds the top-end range established by historical data the system will recalibrate the top-end to maintain a full range for this particular user.

In one embodiment the system utilizes two displays: the first display is integrated within the housing of the accelerometer and/or camera and utilized for control information such as the type of exercise being performed the speed of travel, the video being watched, the time, the time spent exercising, the calories burned, heart rate, percent of goal achieved, etc. The second display is remote to the first display (i.e. In a separate housing from the accelerometer and/or camera) and typically larger than the first display.) In one embodiment, the system establishes a centerline (i.e. center of mass) for head and torso. Having established the centerline (and the amount of motion characteristic with the exercise itself) the system can modulate video presentation as a function of head and/or torso deviating from the centerline when the motion exceeds the motion characteristic with the exercise. Note: In this document a "video presentation or video content" shall include: forward motion video, video games, a slideshow, personal image content, and any other interactive video content presented on a video display. Further note that "interactiveness" can be achieved by intention of the user or passively by the body motions or physiologic activity of the user.

For example in a forward motion video the user may select one of two directions on which to continue the journey by leaning her torso toward the left or the right, with the system modifying the forward motion video accordingly. Similarly, in a game the user may use this functionality to steer a vehicle, an avatar, a cursor, or a paddle which may be used to strike a ball. In one embodiment, the video tracker may identify a group of pixels as hands, thereby allowing an additional input for use in games or directionality. Similarly, the system may be used to navigate viewing digital content such as photographs. Likewise the system may be used to select television shows, or navigate through Facebook. In one embodiment the voice maybe similarly be used.

Because the ambient environment of a gymnasium is often visually dynamic, with people constantly in motion behind the use, it is desirable for the system to be able to reject visual noise in implementations utilizing camera. To this end one embodiment of the system video tracker can characterize the cyclically motile elements within the input from camera as "the user" and subsequent reject motility from other elements. Similarly, in one embodiment the system first identifies which motile elements are the "user" and subsequently tracks other features as they enter the field of view, especially so that as they approach the "user" these non-user elements may continue to be rejected. "Elements" in this case can refer to specific pixels or groups of pixels with relatively non-varying color, darkness, pattern and the like. A further embodiment is for the system to include an assumption algorithm which identifies elements that move together. Due to the proximity of the user to the camera, the largest group of elements is always the "user" and so non-user elements can be identified and ignored.

It is common for users to prefer certain exercise profiles. In one embodiment this includes specific artificial events that require the user to increase or decrease the rate of exercise. In one embodiment this includes forward motion video that includes alternate paths, such as running along the stream or through the forest.

In one embodiment the system includes physiologic data such as heart rate, to modulate the video presentation. In one embodiment heart rate is measured directly by camera.

DESCRIPTION OF DRAWINGS

Like reference symbols in the drawings indicate like elements.

DETAILED DESCRIPTION

Figure 1:
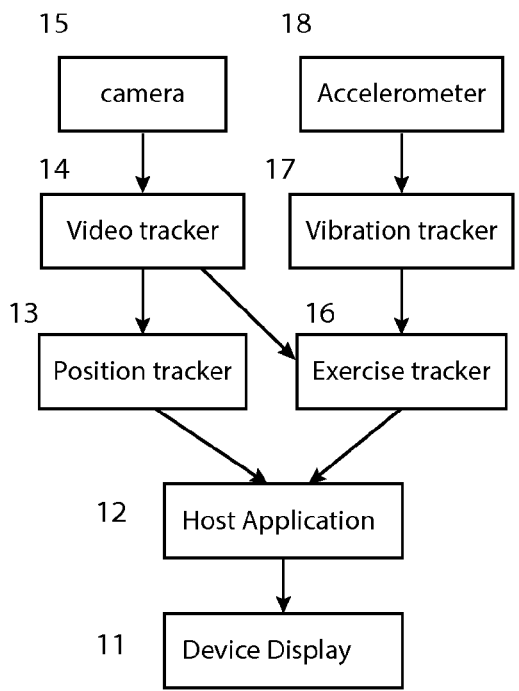
FIG. 1 shows a flowchart for modifying a video presentation by exercise machine.

FIG. 1 shows a generic flowchart of system operation. Video tracking module 14, host application 12, display 20, processor 21, camera 15, user exercise tracker 16 and user position tracker 13 all reside within display device 11. In an alternate embodiment display device 11 includes an accelerometer 18 and vibration tracking module 17 in lieu of or in addition to camera 15 and its associated elements. Display device 11 can be a smartphone, tablet computer, laptop or other kind of computing device as long as it has a camera 15 and/or accelerometer 18 integrally manufactured therein. Host application 12 is software running on display device 11 that accepts inputs from the user position tracker 13 and/or user exercise tracker 16. This input is used to modify video (and associated audio) presented on display device 11.

The video presentation may be forward motion video, mimicking the experience of walking the streets of Paris, hiking through a forest path, swimming underwater, and the like. In such presentations it is desirable to correlate the speed of exercise, such as walking in the case of treadmill, pedaling in the case of bicycle, stroking in the case of rowing, or performing repetition in the case of weightlifting. When the user stops exercise, the video likewise becomes still. The video presentation may likewise be a game such as: a) a race game wherein the user's activity is represented on screen so that exercise rate correlates with speed within the game. Opponents within the game can be synthetic or can be on screen representations of other people exercising; b) a point accumulation game in which the user accumulates points by accomplishing tasks such as steering their character, or the like or c) navigating through a series of stored images, allowing the user to advance (such as by leaning torso to the right), rewind (such as by leaning torso to the left) rotate right (such as by tilting head to the right) and rotate left (such as by rotating head to the left) and deleting images (such as by crossing arms twice). In this manner the user can perform useful and relatively mindless work while exercising. Camera 15 sends motion and position vectors to video tracker 14, which outputs periodicity and "center of mass" data to user position tracker 13 and user exercise tracker 16. User position tracker 13 has an established centerline for the torso and head and can therefore determine if the user is leaning right or left any given time. In an embodiment with a camera 15, user exercise tracker 16 receives periodicity information from video tracker 14 and utilizes knowledge of the exercise machine type (either extrapolated from machine vision or input directly by the user in a setup screen) the system determines an exercise cadence. In a preferred embodiment, the output from the camera is interpreted by the system in its entirety, meaning it is viewing the entire scene simultaneously without differentiation. The system therefore tracks consistent and/or repetitive motion of a large area of adjacent pixels in order to determine cyclical activity. This approach is useful because in most cases the visual surface of the user will constitute the largest region of motile pixels in the frame. Furthermore if the region being tracked falls off the visual surface of the user or if the user steps out of the scene and another replaces them, the tracker will gracefully and seamlessly re-center itself as these conditions remain true. In one embodiment, the system identifies edges and/or regions of motion and tracks those features as user features, such as a head, torso or hand. A further variant of this previous embodiment includes the system tracking motile pixels (e.g. variants in pixel darkness and/or color) that enter the camera view distal to said user features. The system subsequently rejects these motions as extraneous activity such as a trainer or fellow exercise participant walking behind the user.

In one embodiment, the user will tell the system the type of exercise; however, depending on the exercise being performed the small motion periodicity will be vertical or horizontal. In cycling the small motion periodicity is horizontal in orientation whereas on the treadmill and rowing machines, the small motion periodicity is vertical. This data may be used for the system to determine which exercise is being performed. In a preferred embodiment the system relies on the observation that even highly trained athletes have a degree of extraneous motion of their theoretically immobile body parts during exercise. Therefore, exercise tracker 16 is responsible for: a) determining when to trust the periodicity output of the video tracker, and when to apply a correction factor relative to the cadence as a function of what type of exercise is being performed; and b) how to interpret the motion (e.g. horizontal for bikes, vertical for treadmills), and c) if both camera 15 and accelerometer 18 are used in combination, when to defer to the vibrational energy measurement to provide smoother and more responsive exercise output to the host application 12.

In an embodiment utilizing accelerometer 18, vibration tracker 17 correlates data from accelerometer 18 with a lookup table or calculates a value that scales relatively with exercise intensity. When using a treadmill, this signal will have a frequency corresponding to steps per minute.

Figure 2:
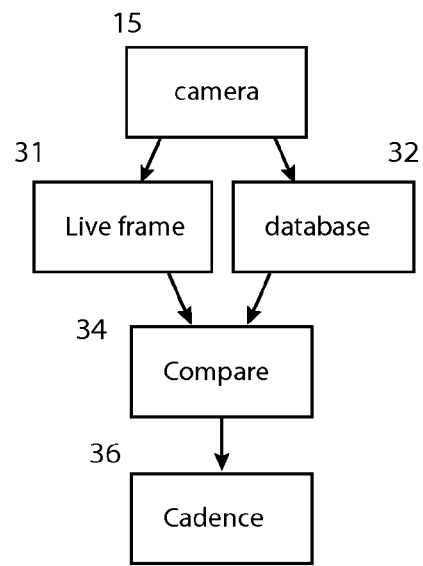
FIG. 2 shows a flowchart of an embodiment for determining cadence.

FIG. 2 shows the input from camera 15 being stored in database 32 as a series of sequential still images, each with a timestamp. Because images are at fixed intervals and sequential is understood that a timestamp may simply be a number in the sequence. At a capture rate of 24 frames per second, each image will be stored with a timestamp varying by 1/24 of a second. Database 32 will typically store at least 2 seconds of still images. At any given instant in time there will be a live frame 31, the frame that most closely represents the action of the user in real time. In step 34, live frame 31 is compared to the frames stored in database 32. In one embodiment pixels are compared for lightness and darkness enabling the system to determine which still image, closest in time to live frame 31 represents a similar pattern to live frame 31 . . . ) In step 36, the timestamp of the image that is closest in time to live frame 31 (and the knowledge of the time between sequential images) is used to determine cadence 36. (i.e The system determines which two still images are closest in time and most similar to each other allows the system to understand the periodicity of motion of the user's activity and is elsewhere described within the application this information is used to determine cadence.)

In one embodiment the system can determine additional resolution by extrapolation. The extrapolation may be performed by artificially creating incremental frames, or by measuring the distance between light and dark pixels of the two approximately similar images and determining an offset (either slightly advanced or slightly decremented), thereby allowing the system to determine the cadence 36 in higher resolution than the capture rate of camera 15.

Figure 3:
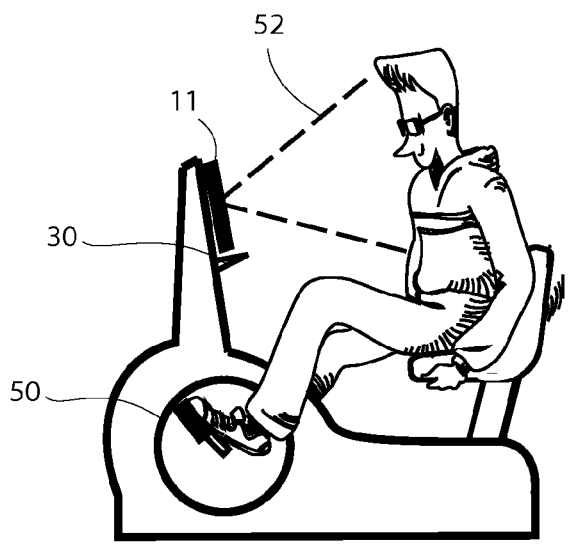
FIG. 3 shows a display device disposed on a cycling exercise machine.

FIG. 3 shows display device 11 temporarily disposed on a shelf 30 that is itself integrally manufactured into cycling exercise machine 50. As shown, shelf 30 may be slanted to appear more like a rack. View region 52 is the view seen by camera 15 and inherent to the manufacture of display device 11 and typically not under user control. View region 52 sees a portion of the user not producing the cadence 36, while the legs are traditionally seen as the body part being exercised (and producing the cadence 36) on this particular machine. View region 52 views a portion of the user that is relatively stationary. In this case the camera 15 is directed to the user's head and torso while the legs are producing cadence 36. Each form of exercise has a characteristic relationship between its visual periodicity and orientation and user cadence 36. In the case of bicycling, video tracker 14 measures the periodicity of small horizontal motions of the user's head and/or torso to determine the cadence 36, which is equal to measured periodicity. Therefore the camera extrapolates exercise cadence while disposed to view away from the machine itself.

Furthermore, the user can indicate leftward motion or a leftward decision to host application 12 by tilting his head and/or torso to the left, as disclosed in FIG. 1. This action may be taken without interrupting exercise and of course may also be done toward the right.

Embodiments using accelerometer 18 are measuring intensity through the vibrational energy transmitted from the user through cycling exercise machine 50 and shelf 30.

Display device 11 adapts between different exercise machines simply by picking it up, resting it on shelf 30 (associated with the machine of interest) and indicating in a "setup" feature within host application 11 the type of exercise machine is being used.

Figure 4:
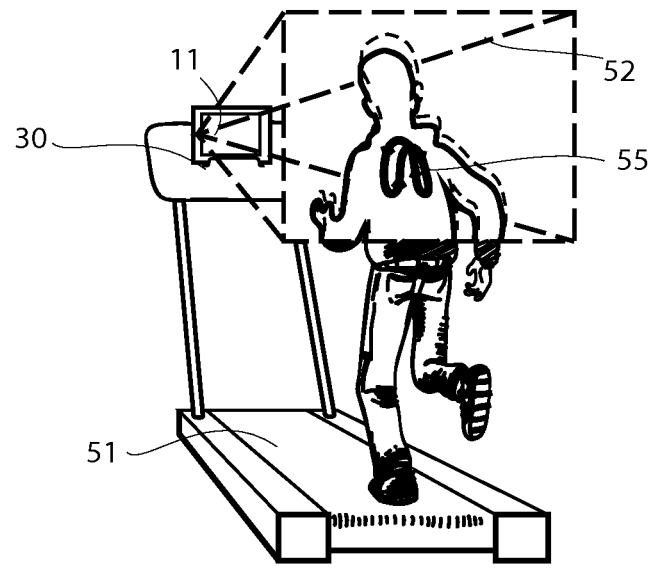
FIG. 4 shows a display device disposed on a treadmill.

FIG. 4 shows display device 11 temporarily disposed on a shelf 30 that is itself integrally manufactured into treadmill 51. As shown, shelf 30 may be slanted to appear more like a rack. As in FIG. 3, view region 52 is inherent to the manufacture of display device 11 and typically not under user control. As in FIG. 3, view region 52 sees a portion of the user not producing the cadence 36, while the legs are traditionally seen as the body part being exercised (and producing cadence 36) on this machine as well. View region 52 sees a portion of the user that is relatively stationary. In this case the camera 15 is directed to the user's head and torso while the legs are producing cadence 36.

Each form of exercise has a characteristic relationship between its visual periodicity and orientation and user cadence 36. In the case of running, in one embodiment, video tracker 14 determines the motion of center of mass 55 of the entire image presented by camera 15 within view region 52 and determines the periodicity of the vertical component to determine the cadence 36, which is equal to one half the measured periodicity. Therefore the camera extrapolates exercise cadence of the user (and the machine) while disposed to view away from the machine itself.

Furthermore, the user can indicate rightward motion or a rightward decision to host application 12 by tilting his head and/or torso to the right, as disclosed in FIG. 1. This action may be taken without interrupting exercise and of course may also be done toward the left.

Embodiments using accelerometer 18 are measuring intensity through the vibrational energy transmitted from the user through cycling exercise machine 50 and shelf 30.

Figure 5:
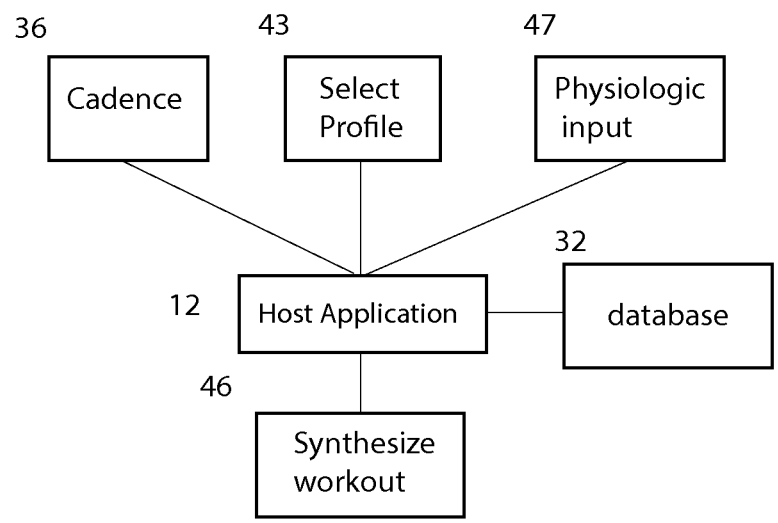
FIG. 5 shows a flowchart for manipulating visual content to provide a desired exercise profile.

FIG. 5 shows an embodiment to allow the user to experience a desired exercise regimen or profile within the context of interactively viewing a video presentation such as forward motion video or a game. It is common for users to prefer certain exercise profiles. An example of such a profile is: a warm-up period, followed by short periods of ever increased intensity interspersed with periods of rest, followed by a cooling down period. Furthermore, each aspect of the profile may have certain time periods associated, such as a 10 min. warm-up, or 30 seconds of intensity followed by 45 seconds of rest, followed by 10 min. of cooling down. To achieve this profile 43 within the context of a video presentation the video is edited to provide scenes that correlate with the experience needed to facilitate the exercise outcome. For example, if the context is a walk through the streets of San Francisco, the video will be modified to include stairs, up hills and down hills, all at the appropriate timing sequence in order to facilitate the desired exercise profile. The video is edited to match the profile desired by the user. This embodiment may also be provided in the game context, by providing a synthesized game in which the gameplay is artificially manipulated to provide the desired exercise profile. While the user perceives the experience as a series of random events it is in fact an experience manufactured to produce a specific exercise profile desired by the user. In one embodiment, the experience is manufactured dynamically as a function of the measured physiology of the user.

For example, in a car race game in which the user is riding a rowing machine (or any other machine) the activities within the race will be modified in accordance with the desired exercise profile. In order to establish a rest period for the user, the system may have one of the other cars (within the video presentation of the game) crash, causing a warning flag to force all racers to slow down, or a dog can come onto the roadway, or a herd of cattle, or the course can become very twisty, or the course may become strewn with damaged car parts, or the terrain may dip steeply downward, etc. As a result of this change in the "story" of the game, the user will slow down until the user's cadence 36 matches the desired exercise profile. Likewise, in order to artificially create the environment in which it would be appropriate for the user to exercise more vigorously, the game may present an uphill stretch, or one of the other "racers" may pass, or whatever obstacle caused the user to slow down is simply removed. Each scenario act as a portion of a visual story that is orchestrated by the system to provide a particular exercise profile. The intent is to provide a system in which the video presentation is sequenced in order to provide a visual and/or storied context that requires the user to increase or decrease the rate of exercise, thereby allowing the user to experience a user-selected exercise profile. In one embodiment this includes forward motion video that includes alternate paths, selectable by the methods explained in FIG. 1.

In one embodiment, the user first selects an exercise profile 43. Database 32 includes the artificial scenarios (such as described above) with which to make the exercise easier or more difficult within the context of the video presentation. The host application 11 synthesizes a presentation based on the profile 46. The "story" options available to alter the level of exercise intensity within database 32. Segments are created to have edits points, allowing the length of a particular segment to be increased or decreased as well as increasing and decreasing the intensity, so that any user profile may be accommodated. The system receives input from cadence 36 simultaneously enabling the user to experience a seemingly random presentation which is in fact enabling the user to experience a particular and desired exercise profile. The system endeavors to randomize the events to make the synthesized presentation appear as natural as possible. In one embodiment, the system further includes physiologic input 47 from the user such as pulse rate, allowing the user to select a desired exercise level in profile 43. In this embodiment the synthesized video 46 is created dynamically, selecting video features from database 32 as a consequence of physiologic input 47. The host application 12 therefore provides a visual experience that is perceived as random exercise to a user that follows a pre-desired exercise profile (selected in step 43) in which the users exercise cadence 36 and/or physiologic input 47 is utilized to manufacture (i.e. edit) a visual experience from video presentation contained within database 32.

The details of implementing the functionality above falls within the abilities of one skilled in the art. Although embodiments of the invention are set forth in the accompanying drawings and the description herein, other features, objects, and advantages of the invention will be apparent from the description and drawings, and from the claims.

We claim:

1. A system to control a video content while the content is viewed during use of one of a plurality of different exercise machines comprising: a display device including a first display in electronic communication with a processor, a sensor in electronic communication with the processor, and a set of machine code adapted for operation on said processor and implemented to modulate the presentation of the video content at least in part as a function of cadence or intensity of user exercise on any of the plurality of different exercise machines, said cadence or user intensity, as determined by data from the sensor, wherein the sensor is a camera.

2. The system of claim 1 wherein the display, the processor, and the sensor are all disposed within the display device.

3. The system of claim 1 further including a second display wherein the second display is disposed external to the device housing and presents the video content.

4. The system of claim 3 wherein the first display provides information to setup and control at least one aspect of the video content.

5. The system of claim 2 wherein the system determines exercise cadence while the camera is disposed with a field of view of the camera is angled predominantly away from one of the plurality of different exercise machines.

6. The system of claim 1 wherein the system utilizes horizontal periodicity data of a cyclist to determines pedal rate data with which to control the video content.

7. The system of claim 1 wherein the system determines vertical periodicity data of an ambulatory user to determine ambulatory rate data with which to the video content.

8. The system of claim 7 wherein ambulatory cadence is a 1:2 ratio with horizontal periodicity and pedaling cadence is a 1:1 ratio with horizontal periodicity.

9. The system of claim 1 wherein the camera determines horizontal periodicity data while viewing the upper half of a user.

10. The system of claim 1 wherein the machine code utilizes an amplitude of horizontal motion in a first direction sensed by the camera that exceeds a displacement of horizontal periodic motion associated with periodicity and utilizes said horizontal motion as user intended input of an action to be associated with the first direction.

11. The system of claim 1 wherein the camera identifies individual pixel groups as hands.

12. The system of claim 1 wherein said machine code determines cadence by comparing entire still images from the camera and associating timing associated with the recordation of each image.

13. The system of claim 12 wherein comparing entire still images includes a determination of two still images closest in time and most similar to each other.

14. The system of claim 1 further including a plurality of still images stored in a database and constantly updated to trail a realtime image by approximately a few seconds, each of said plurality including a timestamp in which cadence is determined by comparing the realtime image to the plurality to determine which of the plurality closest in time is also an approximate visual match to the realtime image, and evaluating the associated timestamp.

15. The system of claim 14 further including an extrapolation performed between the realtime image and at least the associated one of the plurality.

16. The system of claim 1 wherein said set of machine code identifies cyclically motile pixels as the user and subsequently rejects motility from other pixels.

17. The system of claim 1 wherein said set of machine code identifies cyclically motile pixels as the user and subsequently rejects motility originating at the boundaries of camera view range.

18. The system of claim 1 wherein the video content is a game.

19. The system of claim 1 wherein the video content is forward motion video.

20. The system of claim 1 wherein the video content contains visual content personal to the user.

21. The system of claim 19 wherein the system controls forward motion video to continue along one of a plurality of alternatives within a single presentation.

22. The system of claim 18 or 19 wherein the video content is dynamically sequenced to display a series of apparently spontaneous event stimuli to which a logical exercise intensity response to said series results in a predetermined exercise profile.

23. The system of claim 1 wherein the video content is further modulated by physiologic measurement.

24. The system of claim 1 wherein the machine code determines a rate of exercise device operation.

25. The system of claim 1 wherein the camera is extrapolating cadence from small motion periodicity.

26. The system of claim 1 wherein the camera is extrapolating cadence by viewing limbs not producing the cadence.

27. The system of claim 1 wherein ones of the plurality of different exercise machines includes a shelf adapted to hold the display device.

28. The system of claim 1 further including navigating through an entertainment or work environment by gestures including head tilt and torso tilt.

29. A method for providing control over the rate of display of a video content viewed while using an exercise device including the steps of: resting a display device temporarily proximate to one end of the exercise device, said display device to include a display for viewing said video content, a processor, and a camera; directing a view orientation of said camera; establishing at least one visual reference image; measuring a periodicity of motile pixels; and correlating the periodicity with a correlation factor specific to a type of exercise such that the processor may determine the rate of exercise of the user with which to modulate the presentation of display content.

30. The method of claim 29 wherein directing the camera view orientation is entirely determined as a consequence of resting the display device on a shelf integrally manufactured into the exercise device.

* * * * *